United States Patent [19]
Eagles et al.

[11] Patent Number: 5,620,450
[45] Date of Patent: Apr. 15, 1997

[54] TRANSVERSE HINGED DEFORMABLE INTRAOCULAR LENS INJECTING APPARATUS

[75] Inventors: Daniel C. Eagles, Capistrano Beach; Vladimir Feingold, Laguna Niguel; Thomas J. Chamber, Upland, all of Calif.

[73] Assignee: Staar Surgical Company, Inc., Monrovia, Calif.

[21] Appl. No.: 547,295

[22] Filed: Oct. 25, 1995

Related U.S. Application Data

[63] Continuation-in-part of Ser. No. 368,792, Jan. 4, 1995, Ser. No. 345,360, Nov. 18, 1994, Ser. No. 197,604, Feb. 17, 1994, Pat. No. 5,499,987, Ser. No. 196,855, Feb. 15, 1994, and Ser. No. 953,251, Sep. 30, 1992, abandoned.

[51] Int. Cl.⁶ .................................................. A61F 9/00
[52] U.S. Cl. .................................................. 606/107; 623/6
[58] Field of Search ................................ 606/107; 623/6

[56] References Cited

U.S. PATENT DOCUMENTS

| | | | |
|---|---|---|---|
| 4,681,102 | 7/1987 | Bartell | 606/107 |
| 4,919,130 | 4/1990 | Stoy et al. | 606/107 |
| 5,275,604 | 1/1994 | Rheinish et al. | 606/107 |

*Primary Examiner*—Robert A. Hafer
*Assistant Examiner*—Benjamin Koo
*Attorney, Agent, or Firm*—Klima & Hopkins, P.C.

[57] ABSTRACT

A deformable intraocular lens injecting apparatus including a transverse hinge for loading a deformable intraocular lens therein. The transverse hinge connects together two portions of the lens injecting apparatus. A preferred embodiment includes 1) a lens injecting device, 2) a lens cartridge having a transverse hinge, and 3) a nozzle portion. In a most preferred embodiment, the lens cartridge includes a fixed lower tray portion transversely hinged to an upper lid portion.

12 Claims, 8 Drawing Sheets

TRANSVERSE HINGED DEFORMABLE INTRAOCULAR LENS INJECTING APPARATUS

RELATED APPLICATIONS

This is a Continuation-In-Part of U.S. patent application entitled Deformable Intraocular Lens Injection Systems and Methods of Use Thereof, Ser. No. 08/368,792, filed Jan. 4, 1995 (now pending), U.S. patent application entitled "Disposable Intraocular Lens Insertion System", Ser. No. 08/345,360, filed Nov. 18, 1994, (now pending), U.S. patent application entitled "Deformable Intraocular Lens Cartridge, Ser. No. 08/197,604, filed Feb. 17, 1994 (now U.S. Pat. No. 5,499,987), U.S. patent application entitled "Hingeless Lens Cartridges For Insertion Of Deformable Intraocular Lens", Ser. No. 08/196,855, filed Feb. 15, 1994 (now pending), and U.S. patent application entitled "Intraocular Lens Insertion System", Ser. No. 07/953,251, filed Sep. 30, 1992 (abandoned).

FIELD OF THE INVENTION

The present invention is directed to a deformable intraocular lens injecting apparatus for implanting a deformable intraocular lens into the eye. The deformable intraocular lens apparatus according to the present invention includes a transverse hinge to allow a lens holding portion to be opened to receive the deformable intraocular lens and then closed for enclosing the deformable intraocular lens readied for implantation.

BACKGROUND OF THE INVENTION

The deformable intraocular lens and methods of implantation thereof were invented by Dr. Mazzocco in the early 1980's to replace hard-type intraocular lenses. The invention of the deformable intraocular lens substantially reduced the size of the incision into the eye for the insertion of an intraocular lens in the eye. Further, the reduction in size of the incision greatly decreased complications during and after the eye surgery operation, in particular, greatly increasing the rate of healing of the eye and significantly decreasing post-operative astigmatism. The concept of a deformable intraocular lens has been overwhelmingly received by the eye industry and is widely used today.

Operations involving the implantation of a deformable intraocular lens were originally conducted with a forceps for folding the deformable intraocular lens for insertion through the incision in the eye. Around 1986, STAAR Surgical Company, Co. of Monrovia, Calif. introduced the "STAAR Shooter" greatly facilitating the insertion of a deformable intraocular lens through the incision in the eye. Specifically, the "STAAR Shooter" included a longitudinally oriented hinged lens cartridge (i.e., hinged to open sideways), which received the deformable intraocular lens in a flat configuration. The deformable intraocular lens was folded by closing the lens cartridge. The lens cartridge was then loaded into a lens injecting device having a lens cartridge receiver and a plunger for forcing the deformable intraocular lens from the lens cartridge. More specifically, the lens cartridge comprised a lens holding portion and a nozzle portion made as a molded plastic one-piece lens cartridge. The plunger of the lens injecting device forces the folded deformable intraocular lens from the lens holding portion through the nozzle portion having a tip inserted through the incision in the eye, thus, delivering the deformable intraocular lens inside the eye.

Currently, approximately one-half of operations using deformable intraocular lens are still conducted with the use of forceps. However, the acceptance and use of the "STAAR Shooter" and other similar devices, has grown since the introduction of the "STAAR Shooter." It is expected that the trend will continue, and that the use of forceps will eventually cease as new shooter delivery systems and methods are further developed and introduced into the market place.

SUMMARY OF THE INVENTION

A first object of the present invention is to provide an improved deformable intraocular lens injecting apparatus.

A second object of the present invention is to provide a deformable intraocular lens injecting apparatus comprising a transverse hinge to allow a lens holding portion to be opened to receive the deformable intraocular lens and then closed for enclosing the deformable intraocular lens readied for implantation.

A third object of the present invention is to provide a deformable intraocular lens injecting apparatus comprising a lid having a transverse hinge, said lid can be opened and closed for loading a deformable intraocular lens into the lens injecting apparatus.

A fourth object of the present invention is to provide a deformable intraocular lens injecting apparatus comprising a lens injecting device, a transverse hinged lens cartridge, and a nozzle portion.

A fifth object of the present invention is to provide a deformable intraocular lens injecting apparatus comprising a lens injecting device including a lens cartridge receiver and a plunger, a lens cartridge having two portions connected together by a transverse hinge, and a nozzle portion.

The present invention is directed to a surgical device for implantation of a deformable intraocular lens. Specifically, the surgical device is a deformable intraocular lens injecting apparatus including a transverse hinge to allow the apparatus, to be opened and closed to allow the deformable intraocular lens to be loaded into the device for the insertion and implantation operations.

A deformable intraocular lens can be loaded into the lens injecting apparatus in various configurations, however, a flat configuration is particularly preferred. The lens injecting apparatus is preferably designed to be user friendly and easy to load.

The lens injecting apparatus according to the present invention is provided with a transverse hinged closure to allow the lens injecting device to be opened and closed for loading the deformable intraocular lens. The transverse hinge is located between portions or components of the lens injecting apparatus. The lens injecting apparatus can be designed so that both portions are moved to open the lens injecting apparatus, or one portion is held stationery or fixed while the other portion is opened.

Preferred embodiments of the lens injecting apparatus according to the present invention include a transverse hinged closure provided, for example, by a lid, door, swinging access, window, or other related structure that opens to allow the deformable intraocular lens to be loaded in a delivery passageway, and then closed to cover the deformable intraocular lens and define a portion of the delivery passageway.

A preferred embodiment of the present invention involves three separate components including:

1) a lens injecting device;

2) a lens cartridge; and 3) a nozzle portion.

The first component or lens injecting device comprises a lens cartridge receiver and a plunger. A preferred lens injecting device includes a lens cartridge receiver located at one end of the lens injecting device and a slidable plunger. Specifically, one end of the lens injecting device is open and has a recess therein defining a lens cartridge receiver. The recess, for example, can be cylindrical, rectangular, pentagonal, hexagonal, octagonal, etc., or otherwise shaped to conform with the outer surface configuration of the lens cartridge.

The second component or lens cartridge is provided with a transverse oriented hinge to open and close. The preferred lens cartridge comprises two separate portions connected together by a transverse hinge. The transverse hinge has relatively moving components that fit together from each of the portions. Alternatively, the cartridge can be molded as one piece with a "live hinge." A "live hinge" is a hinge that is molded, and does not have to be assembled.

The lens cartridge can be constructed so that both portions of the lens cartridge move, or alternatively, one portion of the lens cartridge is fixed and the other portion of the lens cartridge is moveable. In a more preferred embodiment of the lens cartridge, the bottom portion is fixed and the upper portion is moveable to open like a mouth, for example, of a "crocodile," to greatly facilitate loading of the deformable intraocular lens into the lens cartridge.

In the most preferred lens cartridge, the lower portion can be defined as a lower tray portion and the upper portion can be defined as an upper lid portion wherein the upper lid portion is connected to the lower tray portion by a transverse hinge. The lower tray portion allows the deformable intraocular lens to be loaded into a recess in the lower tray portion. This recess defines a portion of the delivery passageway through the lens cartridge. The upper lid portion may also include a recess or a surface, either defining an upper portion of the delivery passageway through the lens cartridge.

The lower tray portion and the upper lid portion have surfaces that define the delivery passageway through the lens cartridge. One or both of the surfaces can be contoured to facilitate folding of the deformable intraocular lens from a flat configuration into a partially or fully folded configuration. The term folded with respect to the deformable intraocular lens means that the deformable intraocular lens is actually folded, rolled, compressed, or otherwise reduced in outer dimensions when moved through the delivery passageway of the lens cartridge by the plunger of the lens injecting device. In one embodiment, the inner surface of the upper lid portion is contoured for inducing the folding of the deformable intraocular lens. For example, the contour lens shaping surface can be defined by a plurality of longitudinal concave grooves and ridges which tend to fold the outer edges of the deformable intraocular lens both upwardly and inwardly as the deformable intraocular lens is advanced through the delivery passageway of the lens cartridge. A preferred surface contour is defined by three (3) side-by-side longitudinal concave grooves defining a pair of side-by-side folding ridges therebetween.

The third component or nozzle portion connects in some manner with the lens cartridge. Specifically, a delivery passageway through the lens cartridge exits into a delivery passage through the nozzle portion. Preferably, the delivery passageway in the lens cartridge is continuous with the delivery passageway through the nozzle portion. In a most preferred embodiment, the delivery passageway through the lens cartridge tapers inwardly in a direction of movement of the deformable intraocular lens and transitions into an inwardly tapering passageway of the nozzle portion. The smooth transition of the delivery passageways through the lens cartridge into the nozzle portion ensures that the deformable intraocular lens will not be damaged when passing through the transition therebetween.

The three separate components of the deformable intraocular lens injecting apparatus according to the present invention can be connected together when assembled in various manners, for example, preferably the connections are interference or snap fit type connections between the lens injecting device and lens cartridge, and the lens cartridge and the nozzle portion. These connections can be permanent once assembled, and specifically designed to prevent disassembly (e.g., snap fit connections which are not releasable). Alternatively, some or all of the connections can be designed to be purposely separable. Alternatively, threaded-type connections, adhesive connections, heat welded or ultrasonically welded connections, and other types of mechanical fastener-type connections can be implemented alone or in combination to join these components together.

In another embodiment of the present invention, the lens injecting device and the lens cartridge, or a portion of the lens cartridge, can be made as a one-piece unit. For example, the body of the lens injecting device can be made as a one-piece unit with the lower portion of the lens cartridge, and a separate upper portion of the lens cartridge is connected to the one-piece unit by a transverse hinge. In this embodiment, once the deformable intraocular lens is loaded into the lens cartridge portion of the one-piece unit, the nozzle portion is then connected thereto.

In a further embodiment, the lens cartridge, or a portion of the lens cartridge, is formed as a one-piece unit with the nozzle portion. For example, the lower portion of the lens cartridge is molded as a one-piece unit with the nozzle portion, and the upper portion of the lens cartridge is a separate piece connected to the one-piece unit by a live transverse hinge. A deformable intraocular lens can be loaded into the lens cartridge portion and then closed, and this combined assembly is then connected to the lens injecting device.

The delivery passageway through the deformable lens injecting device according to the present invention is preferably configured or contoured for folding the deformable intraocular lens. For example, the delivery passageway can be inwardly tapering (i.e., having a reducing cross-sectional area in the direction of movement of the deformable intraocular lens during the delivery operation). Further, the delivery passageway can be contoured to enhance folding of the lens. For example, one or more grooves can be provided inside the delivery passageway for folding the lens. In a most preferred embodiment, a pair of grooves is provided for bending edges of the deformable intraocular lens upwardly or downwardly from the center plane of the deformable intraocular lens in a flat configuration, and then moving these edges inwardly as the deformable intraocular lens is advanced through the delivery passageway. In this manner, the inwardly tapering feature compresses the deformable intraocular lens while the groove feature modifies the configuration of the lens from its flat configuration to further institute folding and allowing the lens to be further compressed versus a random compression deformable intraocular of the lens which is not as preferable. Specifically, random compressing of the deformable intraocular lens may cause folding in such a manner as to cause high stress and potentially cause damage inside on the surface of the elastic structure of the deformable intraocular lens (e.g., material damage due to shear).

DETAILED DESCRIPTION OF THE PREFERRED EMBODIMENTS

The present invention is directed to a surgical device for implantation of a deformable intraocular lens into the eye. Specifically, the surgical device or deformable intraocular lens injecting apparatus according to the present invention is capable of delivering a deformable intraocular lens through an incision, in particular a small incision (i.e., 5 millimeters or less) made in the eye.

A preferred embodiment of the deformable intraocular lens injecting apparatus surgical device according to the present invention is capable of receiving a deformable intraocular lens in a flat configuration (i.e., unfolded state), and then folding the deformable intraocular lens into a configuration (e.g., folded, rolled, compressed, etc.) allowing the deformable intraocular lens to pass through the incision in the eye. In other embodiments, the deformable intraocular lens can be partially folded or fully folded prior to being loaded into the lens injecting device, or the lens cartridge is configured to partially fold or fully fold the deformable intraocular lens prior to the lens cartridge being loaded into the lens injecting device.

The deformable intraocular lens injecting apparatus according to the present invention can be designed in a variety of different arrangements embodying the common feature of a transverse hinge connecting components or portions of the apparatus allowing a deformable intraocular lens to be loaded in the apparatus, and then closed for enclosing the deformable intraocular lens readied for implantation. Further, the lens injecting apparatus is preferably made of autoclavable plastic (e.g., polysulfone) injection molded components. However, some or all of these components can be made of stainless steel or titanium. Further, the materials and design of the lens injecting apparatus can be selected to allow the lens injecting device to be disposable (i.e., simple design, low materials costs, low assembly costs). The following are preferred embodiments of the present invention.

Figure 1:
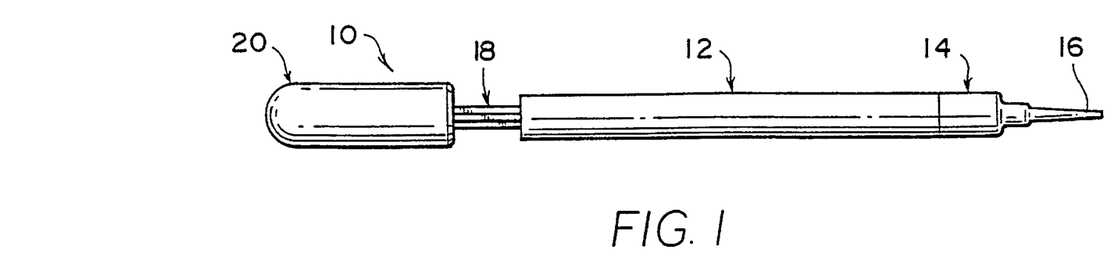
FIG. 1 is a side elevational view of a preferred embodiment of a lens injecting apparatus according to the present invention.

A preferred embodiment of the lens injecting apparatus 10 according to the present invention is shown in FIG. 1. The lens injecting apparatus 10 comprises a lens injecting device 12, nozzle portion 14 having a nozzle tip 16, and a plunger 18. The nozzle portion 14 is connected to the lens injecting device 12, and the plunger 18 is slidably disposed within the body portion 12'. Further, the plunger 18 is provided with a gripping portion 20.

Figure 2:
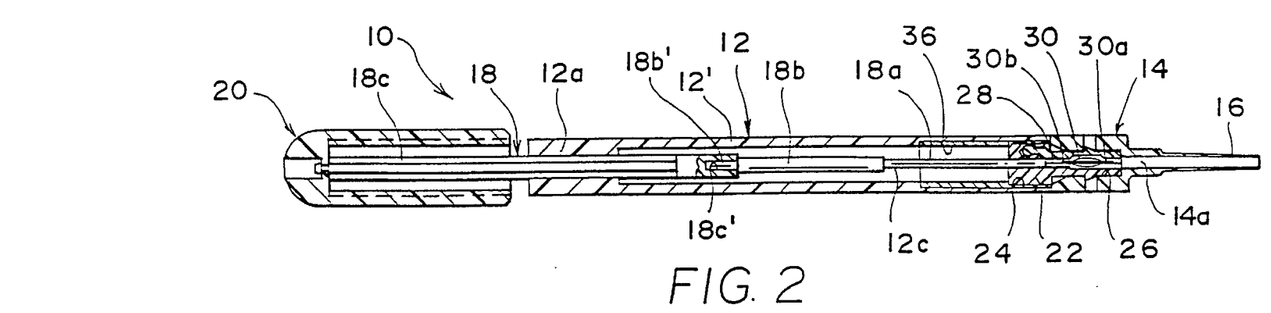
FIG. 2 is a side longitudinal cross-sectional view of the lens injecting apparatus shown in FIG. 1.
Figure 3:
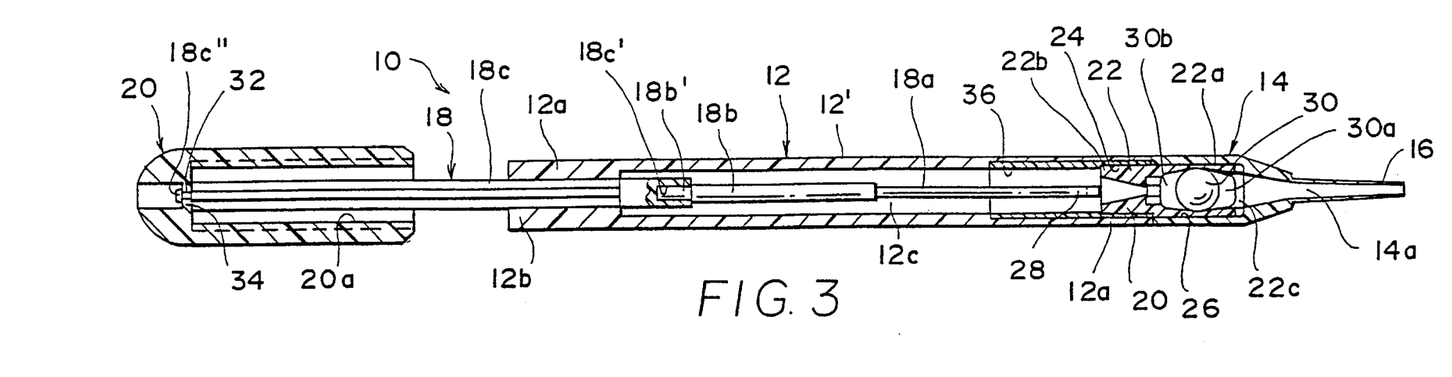
FIG. 3 is a top longitudinal cross-sectional view of the lens injecting apparatus shown in FIG. 1.

Referring to FIG. 2, a lens holding structure such as a lens cartridge 22 is disposed within the lens injecting apparatus 10. The details of the arrangement of the lens cartridge 22 will be described hereinbelow. The lens cartridge 22 is a separate component from the lens injecting device 12 and nozzle portion 14, and is loaded with a deformable intraocular lens prior to being loaded into the lens injecting device 12.

Figure 4:
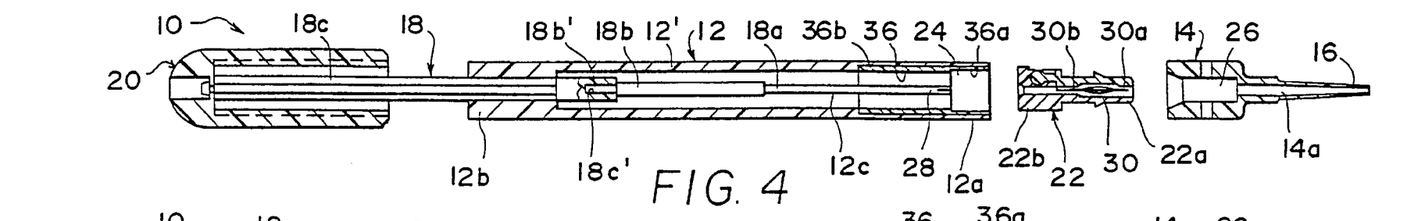
FIG. 4 is a side longitudinal cross-sectional view of the lens injecting apparatus shown in FIG. 1 prior to assembly.

The lens cartridge 22 when loaded into the lens injecting device 12 is disposed within a lens cartridge receiver 24 of the lens injecting device 12 and a lens cartridge receiver 26 of the nozzle portion 14, as shown in FIGS. 2 and 4. Specifically, a front portion 22a of the lens cartridge 22 is located within the lens cartridge receiver 26 of the nozzle portion 14, and a rear portion 22b of the lens cartridge 22 is located within the lens cartridge receiver 24 of the lens injecting device 12.

The plunger 18 comprises a front plunger portion 18a, a middle plunger portion 18b, and a rear plunger portion 18c. The front plunger portion 18a is provided with a slotted tip 28 for receiving the trailing haptic 30b of the deformable intraocular lens 30, as shown in FIG. 2.

The front plunger portion 18a and the middle plunger portion 18b have a one-piece construction (e.g., plastic molded component). The front plunger portion 18a is a cylindrical rod and the middle plunger portion 18b is a cylindrical rod. Further, the front plunger portion 18a has a smaller diameter relative to the middle plunger portion 18b. Alternatively, the cross-sectional shape of the front plunger portion 18a and middle plunger portion 18b can be other than circular (e.g., rectangular, square, star-shaped, oval, cross-shaped, T-shaped, etc.). Further, the front plunger portion 18a and middle plunger portion 18b can have the same shape and cross-sectional size. In a further alternative embodiment, the cross-section size and shape of the front plunger portion 18a can smoothly transition (i.e., not discontinuous such as step-like transition shown) into the middle plunger portion 18b.

The rear plunger portion 18c is a separate component. The rear plunger portion 18c is provided with a cross-sectional shape providing a keyway-type arrangement with the body portion 12' of the lens injecting device 12 to prevent relative rotation therebetween. Specifically, the body portion 12' is provided with a guide 12a having a passageway sized slightly larger than the outer dimensions of the rear plunger portion 18c to allow sliding therebetween, and cross-sectionally shaped to match the cross-sectional shape of the rear plunger portion 18c. In embodiments having interlocking keyway-type cross-sectional shapes of the passageway through guide 12a and rear plunger portion 18c, these arrangements prevent relative rotation between the plunger 18 and body portion 12'.

The plunger 18 is constructed of two separate pieces to facilitate assembly of the lens injecting device 10. The middle plunger portion 18b is provided with an end 18b', which is received within an end 18c'. Specifically, the end 18b' is configured to fit inside a receiver in the end face of the end 18c'. For example, the end 18b' and end 18c' can be configured to interference fit or snap fit together to facilitate assembly. Alternatively, the plunger 18 can have a one-piece construction.

The rear plunger portion 18c is provided with a tip 18c" to connect the gripping portion 20 to the plunger 18. Specifically, the tip 18c" is configured to snap fit into a hole 32 through a flange 34 of the gripping portion 20. This configuration allows the gripping portion 20 to freely rotate relative to the plunger 18. Alternatively, the gripping portion 20 can be fixed to prevent relative rotation between the gripping portion 20 and plunger 18. Even further, the gripping portion 20 and plunger 18 can have a one-piece construction. Still further, the surface of gripping portion 20 may comprise a knurled, textured, slotted or otherwise not smooth surface to enhance gripping friction. Further, the gripping portion 20 may comprise a thumb engaging structure which operates in conjunction with a related finger engaging structure optionally provided on lens injecting device 12.

The gripping portion 20 is provided with a receiver 20a for accommodating the rear end 12b of the lens injecting device 12 when the plunger is advanced forward. In a preferred embodiment, the receiver 20a is threaded to cooperate with one or more protrusions or threads on the rear end 12b to provided threaded advancement of the plunger 18.

The body portion 12' is provided with a cavity 12c for accommodating the plunger 18, and allowing movement of the plunger 18 relative to the lens injecting device 12. Further, the lens cartridge 22 is provided with a passageway 22c leading to a passageway 14a through the nozzle portion 14. The passageway 14a exits at the nozzle tip 16.

Figure 5:
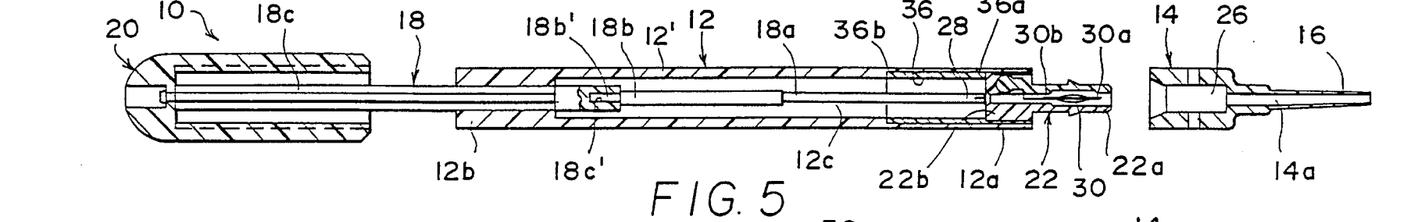
FIG. 5 is a side longitudinal cross-sectional view of the lens injecting apparatus shown in FIG. 1 partially assembled.
Figure 6:
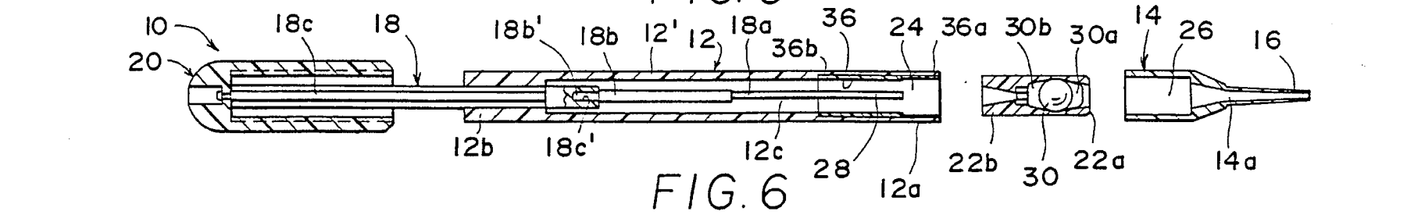
FIG. 6 is a top longitudinal cross-sectional view of the lens injecting apparatus shown in FIG. 1 prior to assembly.
Figure 7:
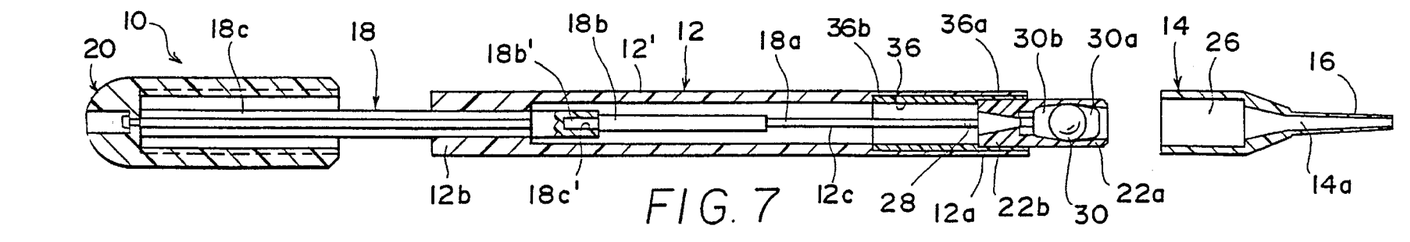
FIG. 7 is a top longitudinal cross-sectional view of the lens injecting apparatus shown in FIG. 1 partially assembled.

The assembly of the lens injecting device 10 is shown in FIGS. 4–7. After the deformable intraocular lens 30 is loaded into the lens cartridge 22, the rear end 22b of the lens cartridge is loaded into the lens cartridge receiver 24 of the lens injecting device 12, as shown in FIGS. 5 and 7. The lens cartridge receiver 24 is defined by an inner sleeve 36 installed within the front end 12a of the body portion 12'. The inner sleeve 36 comprises a front inner sleeve portion 36a and a rear inner sleeve portion 36b. The lens cartridge receiver 24 is configured to provide a locking fit with the rear end 22b of the lens cartridge 22.

After the lens cartridge 22 is loaded into the lens cartridge receiver 24 of the body portion 12', the nozzle portion 14 is connected to the lens cartridge 22. Further, the front end 22a of the lens cartridge 22 is loaded into the lens cartridge receiver 26 of the nozzle portion 14, which snap fit together.

Figure 8:
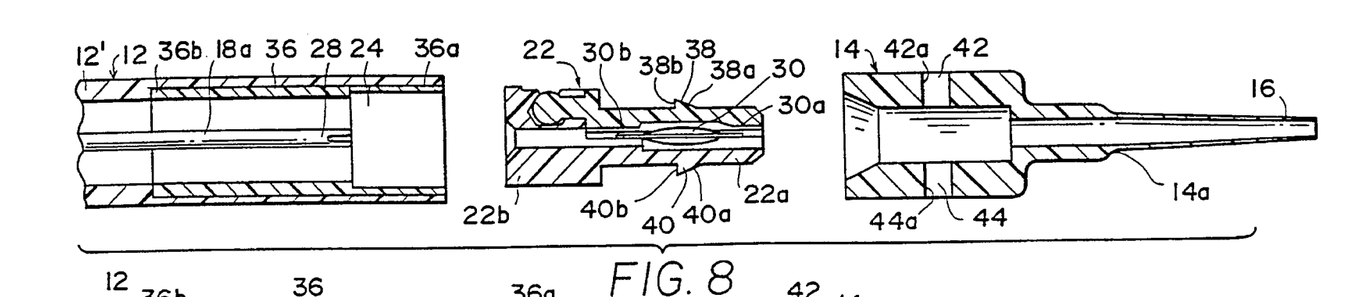
FIG. 8 is a detailed partial side longitudinal cross-sectional view of the lens injecting apparatus shown in FIG. 1 prior to assembly.
Figure 9:
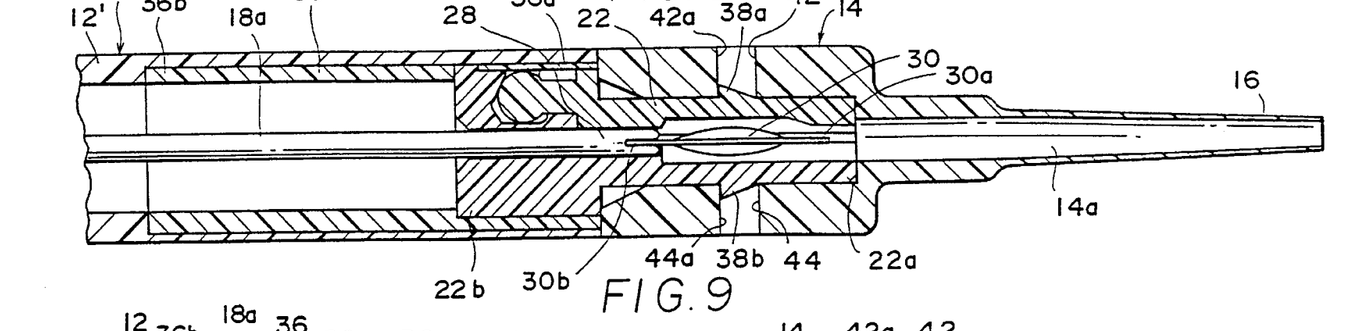
FIG. 9 is a detailed partial side longitudinal cross-sectional view of the lens injecting apparatus shown in FIG. 1 fully assembled.
Figure 10:
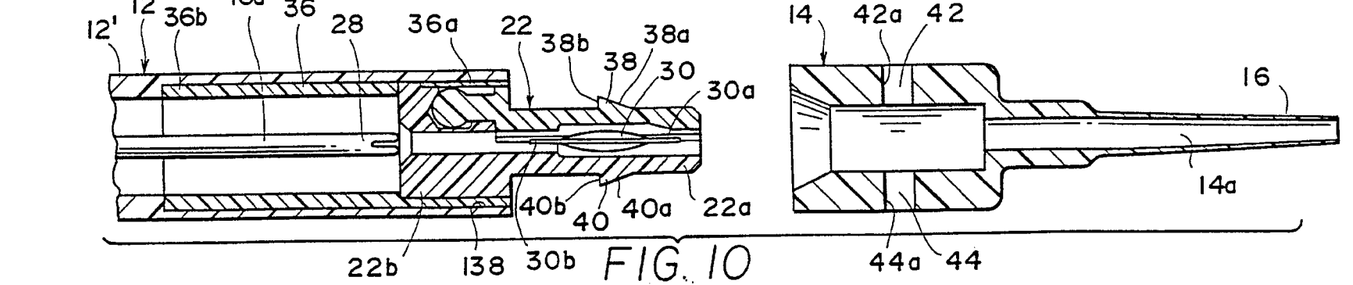
FIG. 10 is a detailed partial side longitudinal cross-sectional view of the lens injecting apparatus shown in FIG. 1 partially assembled.

The details of the connection between the lens cartridge 22 nozzle portion 14 is shown in FIGS. 8–10.

The lens cartridge 22 includes an upper tang 38 and a lower tang 40 cooperating with an upper hole 42 and a lower hole 44, respectively, of the nozzle portion 14. Further, the tangs 38 and 40 are provided with inclined portions 38a and 40a, respectively, to facilitate assembly of the nozzle portion 14 over the front end 22a of the lens cartridge 22. Once the nozzle portion 14 is fully assembled on the front end 22a of the lens cartridge 22, the edges 38b and 40b of the tangs 38 and 40 catch the edges 42a and 44a, respectively, of the holes 42 and 44, as shown in FIG. 9.

Figure 11:
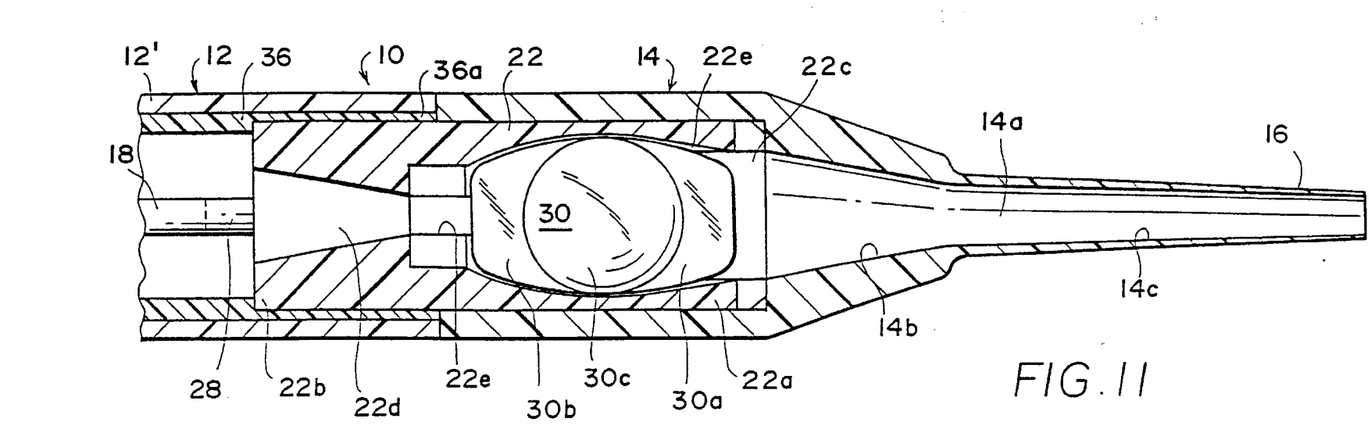
FIG. 11 is a detailed partial top longitudinal cross-sectional view of the lens injecting apparatus shown in FIG. 1 fully assembled with the plunger retracted.
Figure 12:
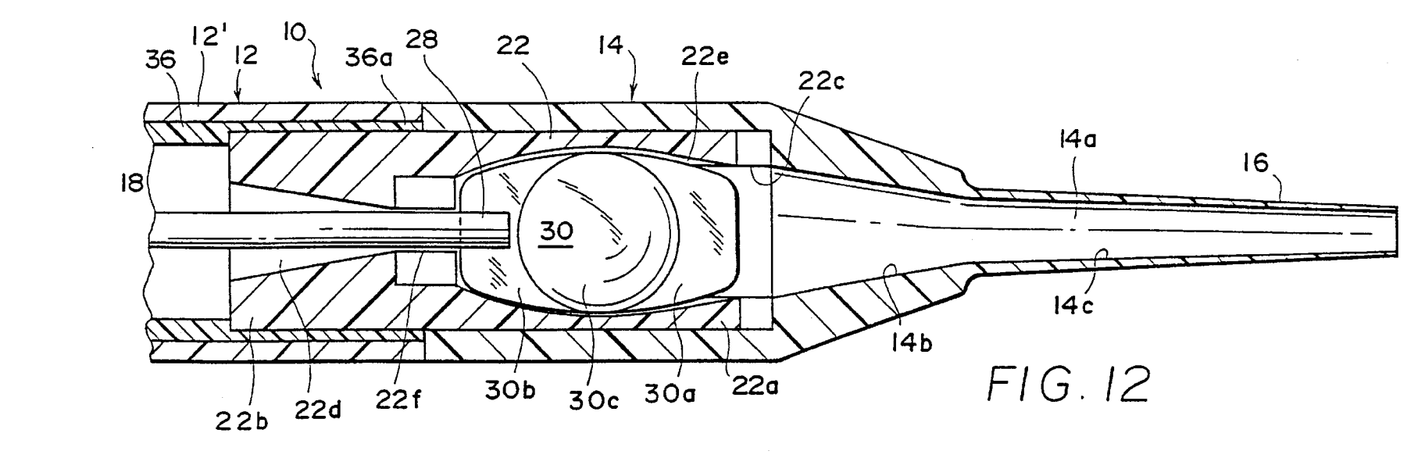
FIG. 12 is a detailed partial top longitudinal cross-sectional view of the lens injecting apparatus shown in FIG. 1 fully assembled with the plunger partially advanced into contact with the deformable intraocular lens.

The details of the manner in which the slotted tip 28 of the plunger 18 makes contact with the deformable intraocular lens 30 is shown in FIGS. 11 and 12. The slotted tip 18 is shown as having a flat end face, however, the end face can be rounded (e.g., convex), recessed (e.g., concave), faceted or other shapes.

The slotted tip 28 is located in the position shown in FIG. 11 after the lens cartridge 22 has been loaded into the lens injecting device 10. During the implantation operation, the slotted tip 28 is advanced forward until the slotted tip surrounds the trailing haptic 30b and contacts or almost contacts the optic portion 30c, as shown in FIG. 12.

The rear end 22b of the lens cartridge 22 is provided with an inwardly tapering (e.g., funnel-shaped) passageway 22d for guiding the slotted tip 28 of the plunger 18 into accurate contact with the deformable intraocular lens 30. The inwardly tapering passageway 22d leads into a lens holding passageway 22e having curved sides to accommodate the deformable intraocular lens in a flat configuration. The lens holding passageway 22e transitions into the passageway 22c of the lens cartridge 22. The passageway 22c transitions into the passageway 14a of the nozzle portion 14. The passageway 14a includes a greater inwardly tapering passageway portion 14b leading into a lesser inwardly tapering passageway portion 14c.

The detailed construction of a preferred lens cartridge 22 for use in the lens injecting apparatus 10 is shown in FIGS. 13–22.

The lens cartridge 22 comprises an upper portion 100 connected to a lower portion 102 by transverse hinge 104. The transverse hinge 104 is a structure involving separate relatively moving components. Various designs and arrangements of the transverse hinge 104 can be substituted for the design shown (e.g., separate pin design), however, designs are somewhat limited due to molding considerations. Alternatively, the transverse hinge 104 can be replaced with an integral molded "live" hinged structure at the cost of increasing the difficulties of molding the lens cartridge.

The transverse hinge 104 is oriented transverse to a center longitudinal axis of the lens injecting apparatus 10. This arrangement allows the lens cartridge 22 to be opened similar to the mouth structure of a "Crocodile", providing easy user friendly loading of the deformable intraocular lens into the lens cartridge 22. The lens cartridge 22 is preferably configured so that the lens cartridge 22 opens in a forward direction as shown in FIG. 13, however, it is possible to modify the configuration so that the lens cartridge opens in an opposite rearward direction.

The transverse hinge 104 is preferably located above the center axis (i.e., off center axis) of both the lens cartridge 22 and lens injecting apparatus 10, again to facilitate loading of the deformable intraocular lens, and to provide the inwardly tapering passageway 22d (See FIG. 11) for accommodating the advancing slotted tip 28 of the plunger 18. Specifically, the location of the transverse hinge 104 is placed above the center location of the passageway 22d to simplify the design and molding technique. Alternatively, the hinge 104 can be located at the center of the height of the lens cartridge 22, however, the passageway 22d would have to be molded through the transverse hinge to allow the slotted tip 22 to pass through the passageway 22d when the lens cartridge is in a closed configuration.

Figure 13:
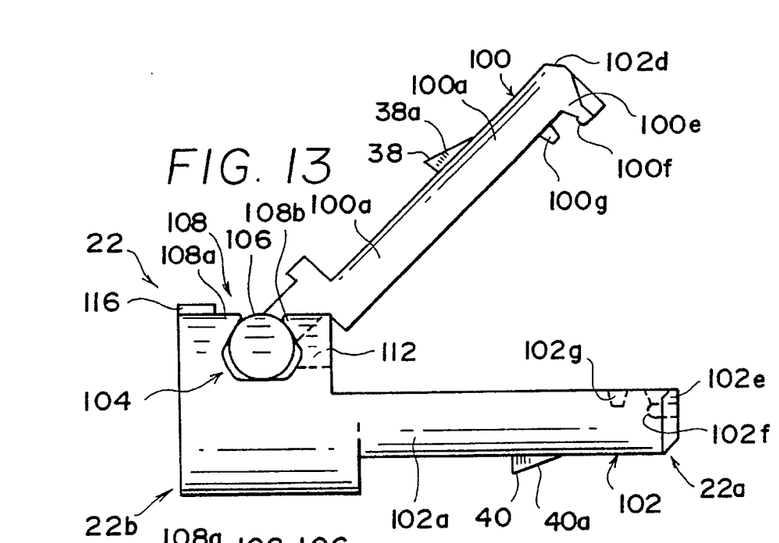
FIG. 13 is a side elevational view of a preferred embodiment of the lens cartridge according to the present invention in an open configuration for receiving a deformable intraocular lens.
Figure 14:
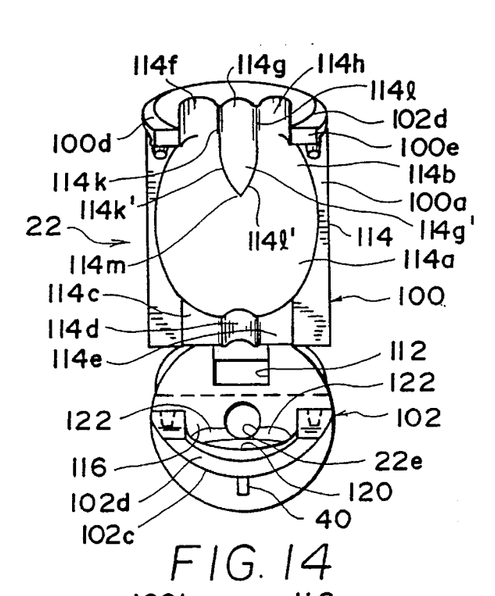
FIG. 14 is a front elevational view of the lens cartridge shown in FIG. 13.

In the embodiment shown in FIG. 13, the upper portion 100 is movable (i.e., functions as a lid) relative to the fixed lower portion 102. This design facilitates loading the deformable intraocular lens, since the orientation (i.e., substantially horizontal) of the lower portion 102 of the lens cartridge 22 remains fixed (i.e., not moving) during the loading operation. However, alternatively, the lower portion 102 can be designed to be movable relative to a fixed upper portion 100, or both the upper portion 100 and lower portion 102 can both be movable.

The transverse hinge 104 in the embodiment shown in FIG. 13, is formed when the upper portion 100 and lower portion 102 are snap fitted together. Specifically, the upper portion 100 comprises a pivot portion 106, which snap fits into a pair of pivot supports 108 provided on the lower portion 102.

The pivot portion 106 is defined by a cylindrical pin-like structure 106a having a pair of ends 106b (See FIG. 17) molded into the upper portion 100. The cylindrical pin-like structure 106a is supported by an elongated connector portion 110 to an upper lid portion 110a of the upper portion 100.

The pivot supports 108 are each defined by a pair of opposed gripping elements 108a, 108b for gripping one end 106b of the pivot portion 106. The gripping elements 108a, 108b are molded above a lower tray portion 102a of the lower portion 100. The upper portion 100 is also molded with a recess 112 (See FIGS. 13 and 14) to accommodate the elongated connector portion 110 of upper portion 100. In addition, the lower portion 100 is molded with the passageways 22d and 22e (See FIGS. 11 and 14) to accommodate the slotted tip 28 of the plunger 18.

Figure 15:
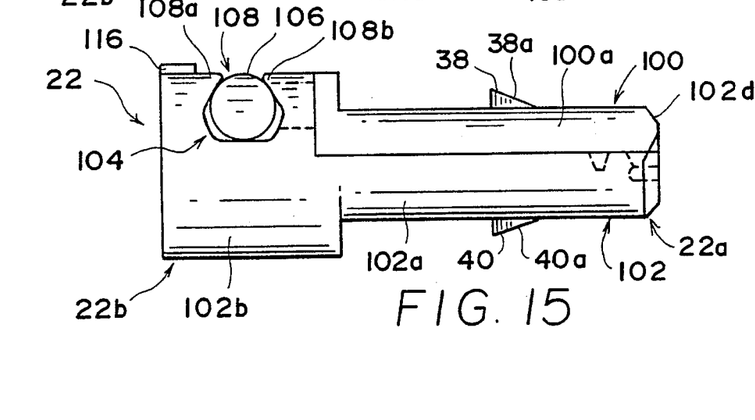
FIG. 15 is a side elevational view of a preferred embodiment of the lens cartridge according to the present invention in a closed configuration after a deformable intraocular lens has been loaded into the lens cartridge.

The exterior shape (i.e., contour) of the lens cartridge 22 includes a faceted front end 22a and a cylindrical rear end 22b, as shown in FIG. 15. Specifically, the bottom portion 102 of the lens cartridge 22 includes a cylindrical base portion 102b (See FIGS. 15 and 16) for being accommodated within the cylindrical-shaped lens cartridge receiver 24 of the inner sleeve 36 of the body portion 12'. The upper lid portion 100a of the upper portion 100 is provided with a flat top surface 100b (See FIG. 16), cylindrical side surfaces 100c, and conical surface 100d (i.e., beveled surface) while the lower tray portion 102a of the lower portion 102 is provided with a cylindrical bottom and side surface 102c and a conical surface 102d for being accommodated within the faceted-shaped lens cartridge receiver 26 of the nozzle portion 14. The conical surface 100d is continuous with conical surface 102d to provide a bevel edge to facilitate assembly.

The upper lid portion 100a of the upper portion 100 is provided with a pair of latch portions 100e cooperating with a pair of latch portions 102e of the lower portion 102. The latch portions 100e comprise protrusions 100f interlocking with recesses 102f of the lower portion 102. This arrangement allows the upper portion 100 to be securely connected to the lower portion 102 prior to loading into the injecting device 12. This arrangement also allows the lens cartridge 22 to be reopened (i.e., a releasable connection) for inspection of the loaded or reloaded deformable intraocular lens.

Further, the upper lid portion 100a of the upper portion 100 is provided with a pair of alignment guides 100g (e.g., pins) cooperating with alignment recesses 102g in the lower tray portion 102b for properly aligning the upper portion 100 with the lower portion 102 when the lens cartridge 22 is closed. The alignment guides 100g and alignment recesses are optional, and can be eliminated in some designs.

The interior shape of the lens injecting device 10, in particular the contours of the surfaces of the lens delivery passageways through the lens cartridge 22 and nozzle portion 14 are particularly important for proper delivery of the deformable intraocular lens. Specifically, the lens delivery passageway is contoured to change the state of the deformable intraocular lens from a flat configuration to a fully folded configuration as the deformable intraocular lens is advanced through and along the delivery passageway.

The upper lid portion 100a of the upper portion 100 is provided with a recess 114 (See FIGS. 14 and 18) defined by a slight convex surface 114a. The recess 114 accommodates an upper portion of the deformable intraocular lens when the lens cartridge 22 is closed.

The upper lid portion 100a also has a center concave groove 114g aligned with the center longitudinal axis of the lens injecting device. Center concave groove 114g is located at the front end of the upper lid portion 100a. A pair of side concave grooves 114f and 114h are positioned side-by-side with center concave groove 114g. Side concave grooves 114f and 114h are also aligned parallel with the center longitudinal axis of the lens injecting device.

Also included in the upper lid portion 100a is a tapered concave groove 114g', which is contiguous with center concave groove 114g at its front end. At its rear end, tapered concave groove 114g' tapers to a point 114m within recess 114. The recess 114 transitions into the set of longitudinal grooves 114f, 114g (114g'), 114h in the direction of the advancing deformable intraocular lens.

The front set of concave grooves 114f, 114g, 114h define a pair of ridges 114k and 114l, which are contiguous with a pair of curvilinear edges 114k' and 114l' defined by tapered concave groove 114g'. The curvilinear edges 114k' and 114l' end at rear point 114m within recess 114. The ridges 114k and 114l and the curvilinear edges 114k' and 114l' function to fold the deformable intraocular lens as the lens is advanced in the direction of implantation.

The upper portion 100 is provided with an alignment key 116 for accurately locating the lens cartridge 22 in the lens cartridge receiver 24 of the lens injecting device 12. The alignment key 116 cooperates with a keyway in the lens cartridge receiver to be described below to prevent relative rotation between the lens cartridge 22 and lens injecting device 12.

Figure 20:
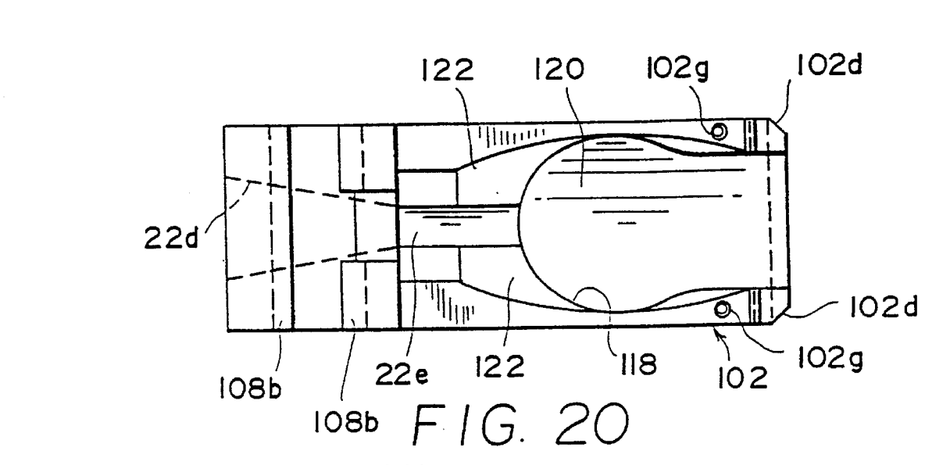
FIG. 20 is a top planar view of the bottom portion of the lens cartridge shown in FIG. 15.
Figure 21:
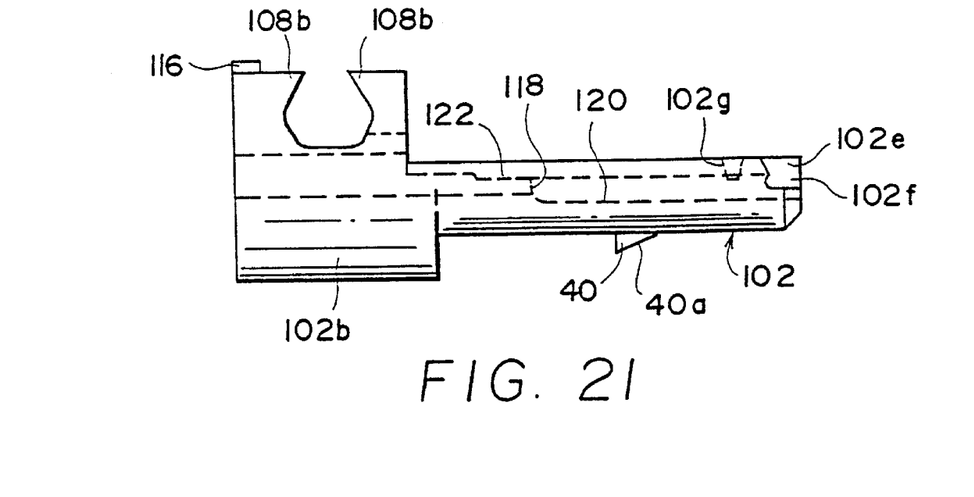
FIG. 21 is a side elevational view of the bottom portion of the lens cartridge shown in FIG. 20.
Figure 22:
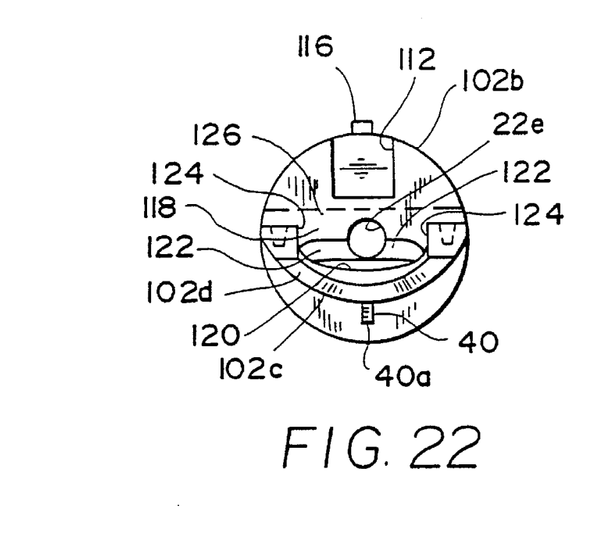
FIG. 22 is a front elevational view of the lens cartridge shown in FIG. 15.

The lower portion 102 is provided with a recess 118 defined by a flat surface, a contoured surface 122, stepped side surfaces 124, and end surface 126 (See FIGS. 20 and 22). These surfaces define a lower portion of the delivery passageway through the lens cartridge 22.

Figure 23:
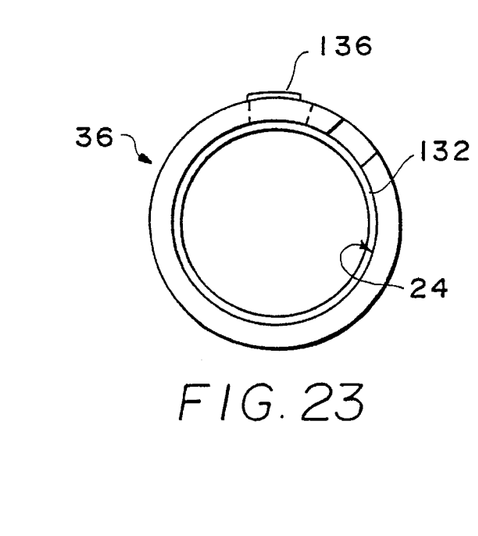
FIG. 23 is a front elevational view of the inner sleeve to be installed within the body portion of the lens injecting device shown in FIG. 2.
Figure 24:
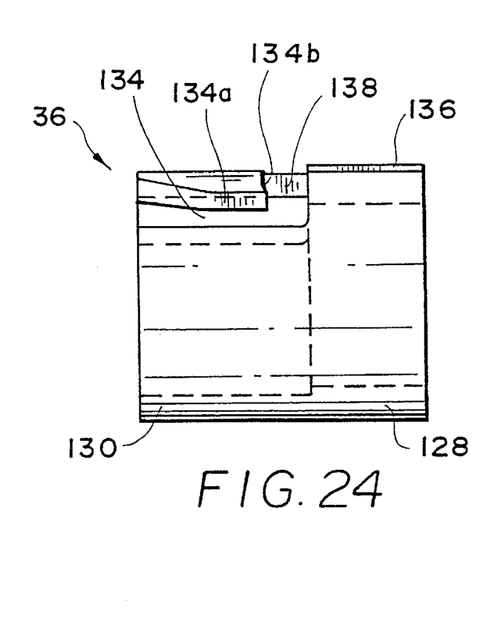
FIG. 24 is a side elevational view of the inner sleeve shown in FIG. 23.
Figure 25:
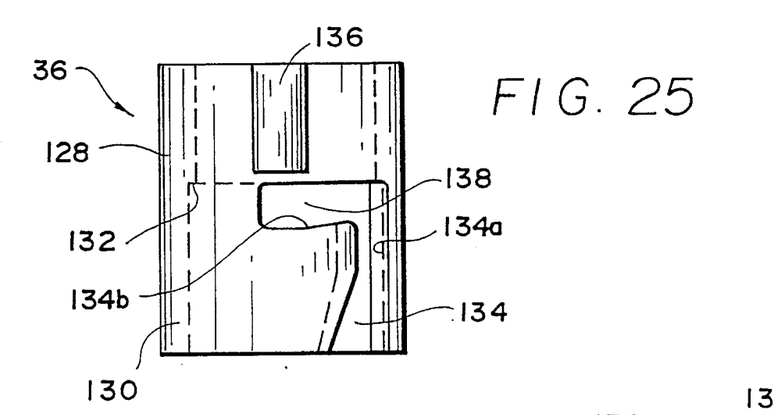
FIG. 25 is a broken away top elevational view of the inner sleeve shown in FIG. 25.

The lens cartridge receiver 24 of the lens injecting device 12 is provided by inner sleeve 36, as shown in FIGS. 8–10. Detailed views of the inner sleeve 36 are shown in FIGS. 23–25.

The inner sleeve 36 is provided with a cylindrical portion 128 having a thicker cross-sectional wall thickness and a cylindrical portion 130 having a thinner cross-sectional wall thickness. Both cylindrical portions 128 and 130 have the same outer diameter but different inner diameters. The cylindrical portion 130 defines a collar for receiving the rear end 22b of the lens cartridge 22. An inner edge 132 is provided at the transition between the cylindrical portion 128 and cylindrical portion 130. The inner edge 132 serves as a stop when the lens cartridge 22 is loaded into the lens cartridge receiver 24.

Figure 16:
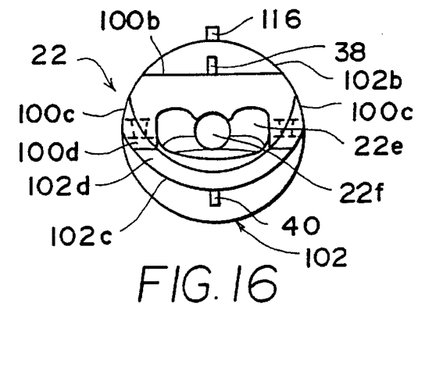
FIG. 16 is a front elevational view of the lens cartridge shown in FIG. 15.
Figure 17:
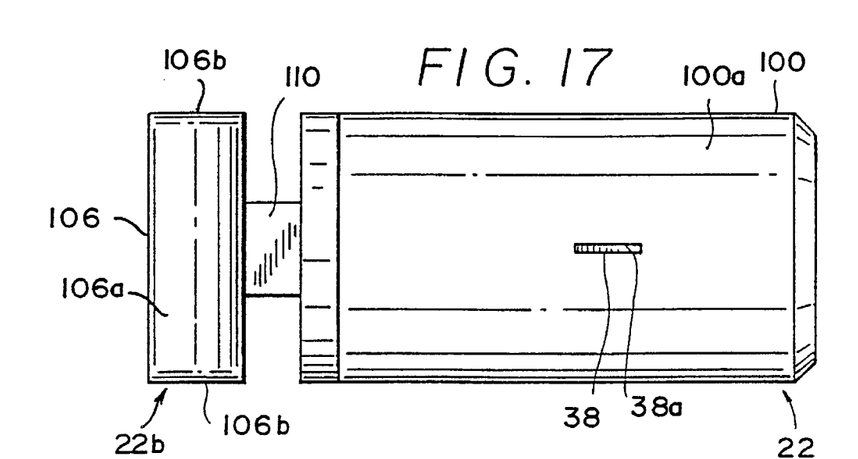
FIG. 17 is a top planar view of a top portion of the lens cartridge shown in FIG. 15.
Figure 18:
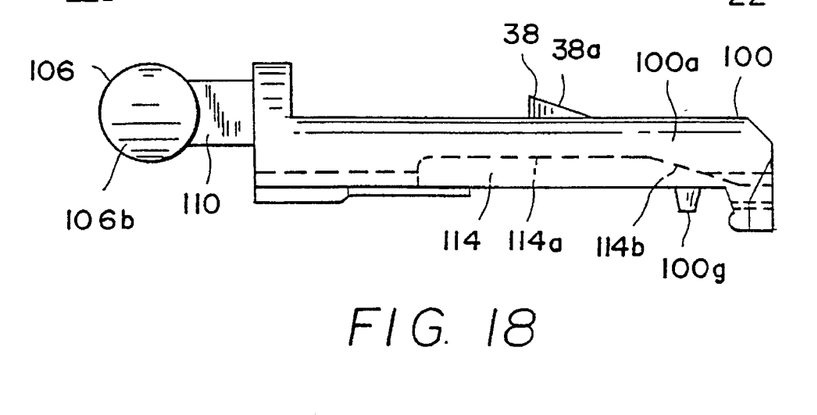
FIG. 18 is a side elevational view of the top portion of the lens cartridge shown in FIG. 17.
Figure 19:
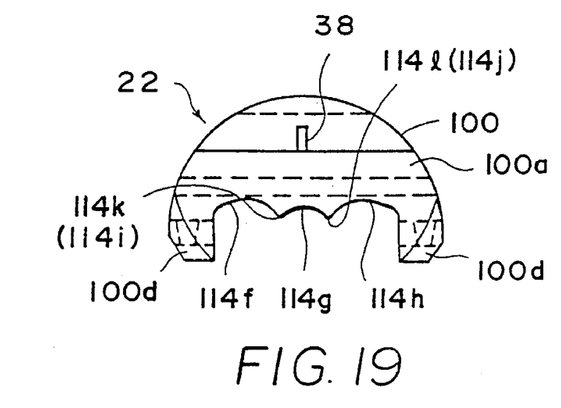
FIG. 19 is a front elevational view of the top portion of the lens cartridge shown in FIG. 17.

The cylindrical portion 130 is provided with a keyway 134 comprising a longitudinal keyway portion 134a extending into a transverse keyway portion 134b for accommodating the key 116 of the lens cartridge 22, as shown in FIG. 16. This arrangement provides a locking arrangement when the lens cartridge 22 is pushed in and then rotated (i.e., a bayonet type locking configuration). Further, the inner sleeve 36 is provided with a key 136 (FIG. 23) to cooperate with a keyway 138 provided in the bottom of the lens injecting device 12 at the lens cartridge receiving end, as shown in FIG. 10).

In the preferred embodiment shown, the transverse hinge of the lens cartridge 22 is positioned inside the lens cartridge receiver 24 of the lens injecting device 12 when assembled together, as shown in FIG. 9. This arrangement prevents the lens cartridge 22 from being opened once inserted into the lens cartridge receiver 24 of the lens injecting device 12. Alternatively, the lens cartridge can be designed so that the transverse 104 is still operable when loaded into the lens cartridge receiver 24 (e.g., the rear portion 22b of the lens cartridge 22 can be lengthened so that the transverse hinge 104 does not enter into the lens cartridge receiver 24 when assembled.

Operation

A deformable intraocular lens is loaded into the lens cartridge 22 when the lens cartridge 22 is in an open mode. The lens cartridge 22 can be either partially connected or disconnected to the lens injecting device 12 at the time of loading.

In the event that the lens cartridge 22 is not yet connected to the lens injecting device 12, then the loaded lens cartridge 22 is loaded into the lens cartridge receiver 24 of the lens injecting device 12. In the event the lens cartridge 22 is partially connected to the lens injecting device 12, the lens cartridge 22 is pushed further into the lens cartridge receiver 24 of the lens injecting device 12.

The tip 6 of the nozzle portion 14 is then placed through the incision made in the eye, and then the plunger 18 is actuated by a user pressing on the gripping portion 20 while holding the body portion 12'. The tip 28 of the plunger 18 is forced into the delivery passageway of the lens cartridge 22, which then forces and advances the deformable intraocular lens along the delivery passageway through the nozzle portion 14 and out of the tip 16 thereof.

We claim:

1. A surgical apparatus for implantation of a deformable intraocular lens through a small incision in the eye, comprising:

a lens injecting device including a slidable plunger and a lens cartridge receiver;

a lens cartridge having a lens delivery passageway therethrough, said lens cartridge having a rear portion disposed within said lens cartridge receiver of said lens injecting device, said lens cartridge including a front portion with an upper lid portion and a lower tray portion, said upper lid portion connected to said lower tray portion by a transverse hinge oriented transversely relative to said lens delivery passageway to allow the lens cartridge to be opened and closed for loading the deformable intraocular lens into said lens cartridge;

a nozzle portion including a lens cartridge receiver accommodating said front portion of said lens cartridge receiver, said nozzle portion when assembled onto said front portion of said lens cartridge maintaining said upper lid portion and said lower tray portion in a closed configuration, said nozzle portion including a lens delivery passageway continuous with said lens delivery passageway of said lens cartridge; and a locking arrangement between said lens injecting device and said lens cartridge engaging, when said lens cartridge is loaded into said lens cartridge receiver of said lens injecting device.

2. An apparatus according to claim 1, wherein said locking arrangement engages when said lens cartridge is rotated relative to said lens injecting device.

3. An apparatus according to claim 1, wherein said locking arrangement engages when said lens cartridge is moved in a direction towards said lens injecting device and then rotated.

4. An apparatus according to claim 3, wherein said locking arrangement is defined by a key located on said lens cartridge cooperating with a bayonet type slot is said lens cartridge receiver of said lens injecting device.

5. An apparatus according to claim 4, wherein said lens cartridge receiver of said lens injecting device includes a sleeve provided with said bayonet type slot, said sleeve being disposed within an end portion of said lens injecting device.

6. An apparatus according to claim 5, wherein said sleeve is provided with a key cooperating with a keyway in said end portion of said lens injecting device to prevent relative rotation therebetween.

7. An apparatus according to claim 1, wherein said lower tray portion is fixed and said upper lid portion is movable about said transverse hinge.

8. An apparatus according to claim 1, wherein said upper lid portion is provided with a plurality of side-by-side grooves for folding the deformable intraocular lens as the deformable intraocular lens is advanced through the lens delivery passageway.

9. An apparatus according to claim 8, wherein said plurality of side-by-side grooves include three side-by-side longitudinal concave grooves defining a pair of ridges.

10. An apparatus according to claim 9, wherein said longitudinal concave grooves are located in a front portion of said upper lid portion.

11. An apparatus according to claim 9, wherein said ridges are contiguous with a pair of converging curvilinear edges defining a center longitudinal concave groove.

12. An apparatus according to claim 1, wherein said lower tray portion is provide with a lens receiving recess.

* * * * *

UNITED STATES PATENT AND TRADEMARK OFFICE
CERTIFICATE OF CORRECTION

PATENT NO. : 5,620,450
DATED : April 15, 1997
INVENTOR(S) : Daniel C. EAGLES et al.

It is certified that error(s) appears in the above-identified patent and that said Letters Patent is hereby corrected as shown below:

Change the third inventor's name as follows:

Change "Chamber" to --Chambers--.

Signed and Sealed this

Thirtieth Day of June, 1998

*Attest:*

BRUCE LEHMAN

*Attesting Officer*     *Commissioner of Patents and Trademarks*